(12) United States Patent
Schön et al.

(10) Patent No.: US 6,282,947 B1
(45) Date of Patent: Sep. 4, 2001

(54) ARRANGEMENT FOR MONITORING THE USEFUL PROPERTIES OF FLUIDS

(75) Inventors: Otmar Schön, Bexbach; Manfred Tumbrink, Bad König; Bernhard Kirsch, Mandelbachtal, all of (DE)

(73) Assignee: Hydac Filtertechnik GmbH, Sulzbach (DE)

( * ) Notice: Subject to any disclaimer, the term of this patent is extended or adjusted under 35 U.S.C. 154(b) by 0 days.

(21) Appl. No.: 09/180,954
(22) PCT Filed: Jun. 28, 1997
(86) PCT No.: PCT/EP97/03393
  § 371 Date: Nov. 18, 1998
  § 102(e) Date: Nov. 18, 1998
(87) PCT Pub. No.: WO98/01750
  PCT Pub. Date: Jan. 15, 1998

(30) Foreign Application Priority Data

Jul. 9, 1996 (DE) .............................. 196 27 587

(51) Int. Cl.⁷ .............................. G01N 11/00; G01M 19/00
(52) U.S. Cl. .............................. 73/53.01; 73/168
(58) Field of Search .............................. 73/53.01, 152.19, 73/152.22, 168; 702/52; 341/51; 356/339

(56) References Cited

U.S. PATENT DOCUMENTS

| | | | |
|---|---|---|---|
| 3,936,192 | * 2/1976 | Skala | 356/339 |
| 4,483,189 | * 11/1984 | Seal | 73/152.22 |
| 4,501,143 | * 2/1985 | Prior et al. | 73/152.19 |
| 4,510,800 | * 4/1985 | Prior | 73/152.22 |
| 4,546,649 | * 10/1985 | Kantor | 73/168 |
| 5,051,921 | * 9/1991 | Paglione | 702/52 |
| 5,686,913 | * 11/1997 | Coln et al. | 341/51 |

FOREIGN PATENT DOCUMENTS

| | | |
|---|---|---|
| 0435713 | 7/1991 | (EP) . |
| 63285467 | 11/1988 | (JP) . |
| 90/06500 | 6/1990 | (WO) . |

* cited by examiner

Primary Examiner—Hezron Williams
Assistant Examiner—Jay L. Politzer
(74) Attorney, Agent, or Firm—Roylance, Abrams, Berdo & Goodman, L.L.P.

(57) ABSTRACT

An arrangement monitors the useful properties of pressure fluids (5) in fluid-technical installations. A plurality of measured variables, each representing a useful property of the pressure fluid, are determined by a plurality of sensors (13, 15, 17) which are combined with a pump (11) to form a structural unit which can be build into a tank (3) containing the pressure fluid. The sensors (13, 15, 17) are hydraulically connected in series with the pump (11).

8 Claims, 3 Drawing Sheets

ARRANGEMENT FOR MONITORING THE USEFUL PROPERTIES OF FLUIDS

FIELD OF THE INVENTION

The present invention relates to an arrangement for monitoring the useful properties of fluids, particularly of pressure fluids in fluid-technical installations. The arrangement has a testing device by means of which a test volume of the fluid can be removed from the container holding it and can be fed to a sensor device. The sensor device includes a plurality of sensors to make and evaluate certain variable measurements, each representing a useful property of the fluid.

BACKGROUND OF THE INVENTION

With operation of fluid-technical installations, the monitoring of certain properties of the pressure fluid for evaluating the usefulness of the fluid and for controlling and monitoring of assemblies of machines and the like is of great importance. The evaluation serves for the maintenance of the properties in a state useful for operation of the fluid-technical installations When a fluid property falls below or exceeds certain boundary values, such property can negatively influence the adaptability for use in a fluid-technical installation during operation. The properties can include, among others:
   a) contamination of the fluid with solids;
   b) greasing or lubricating properties of the fluid;
   c) impurities in the fluid in the form of other substances causing corrosion, especially water;
   d) content of decomposition or degradation products in the fluid, causing oxidation, which negatively influences the usefulness by aging the fluid; and
   e) fluid supply state of the pumps and/or assemblies of machines, in other words the fill level in the fluid container (the fluid level is referenced in the present framework as a useful property).

In case a circumstance or condition arises during operation which endangers the operational capacity of the relevant installation, automatic measures are to occur to avoid or overcome the problem (for instance switching on the cooling machinery). Alternatively, the operation of the installation must be modified or adjusted to avoid damage In any case, it is critical that the operator be informed of the occurrence of any disturbance, that some protocol take places and that an alarm be triggered.

When a test monitoring of the useful properties of fluids is carried out in a more or less automated manner and an analysis of the test volume is undertaken in the laboratory, an incomplete evaluation of the usefulness of the properties can result This is because the analyses and measurements which are carried out are comparable with one another only when the measurements are collected simultaneously at the different measuring sites. In other words, the sites of the test samplings are in definite space and time relationships to one another With two differently timed and cyclical variable test samples, it cannot be guaranteed that they are taken at the same measurement site A same-time measurement showing two different magnitudes at different sites in the system is affirmable if no gradients are present, for example pressure and temperature gradients.

To avoid this problem, a monitoring arrangement is disclosed in JP-A-63285467. The connection of the sensors with the fluid pump allows the same fluid current flows through both of them. On the basis of one test sample at one single measurement site, a continuous evaluation of different measurements relative to one can be guaranteed, and the same fluid current can pass through a plurality of sensors. A virtually error-free monitoring of the properties of the fluid regarding their usefulness is thus possible.

SUMMARY OF THE INVENTION

Objects of the present invention are to provide an arrangement for monitoring useful fluid properties that is characterized by a simple and especially compact construction.

The foregoing objects are basically obtained by an arrangement for monitoring useful fluid properties comprising a container containing a fluid to be monitored and having a container opening. A tubular frame extends through the container opening and into the container for immersion in the fluid. The frame has frame openings for the fluid to pass therethrough. A fluid pump with a driving motor is mounted on the frame and immersed in the fluid. A sensor block houses and integrates a plurality of fluid property sensors and flow channels connecting the sensors in series with one another, and with the fluid pump. The sensor block is mounted on the frame and immersed in the fluid. A sensor attachment plate bar is arranged within the frame, carries an electronic assembly for processing signals from the sensors, and is immersed in the fluid.

The entire testing or mounting arrangement is combined in one unit on the frame, including the sensor attachment plate bar with the electronic assembly processing the sensor signals, is constructed for a method of operation immersed in the fluid, and can be immersed directly in the fluid container. Thus, the measurements required for the monitoring can be evaluated with greater precision and with the smallest possible space requirement for the arrangement.

The series-connection arrangement, with the fluid stream to be tested flowing through the sensor block, preferably includes a particle sensor with integrated opacity measurement for determination of the particle concentration, a viscometer, and a moisture sensor with integrated NTC-resistance, in order, to measure both the free water content therein and also the temperature of the fluid.

With use of a viscometer in the form of a friction wheel viscometer with integrated brake coil, it is advantageously possible to evaluate not only the viscosity of the test fluid stream but also its flow rate. This sensor also facilitates measurement of magnitudes which are sensitive to the rate of flow and facilities control of the function of the monitoring device.

Since the sensor attachment plate bar along with the electronic assembly processing the sensor signals is immersed in the fluid, an evaluation of the dielectric constant of the fluid can be obtained by means of a interdigital capacitor Such capacitor can be provided on the plate bar, directly in contact with the fluid. The corrosion effect of the fluid on copper can be avoided with the aid of an interdigital capacitor of copper-conductor strips.

The signals from the sensors picked up by the electronic assembly are preferably digitized and converted into standardized primary data. Such data is compatible across systems, can be detected by some sort of data terminals and can be processed. Such an arrangement is suitable for the special direct control of auxiliary assemblies for influencing the state of the fluid, for example, by subsidiary flow cooling or heating elements, subsidiary flow filter for the removal of water, and rinsing and cleaning pumps.

Other objects, advantages and salient features of the present invention will become apparent from the following detailed description, which taken in conjunction with the annexed drawings, discloses a preferred embodiment of the present invention.

BRIEF DESCRIPTION OF THE DRAWINGS

Referring to the drawings which form a part of this disclosure.

DETAILED DESCRIPTION OF THE INVENTION

Figure 1:
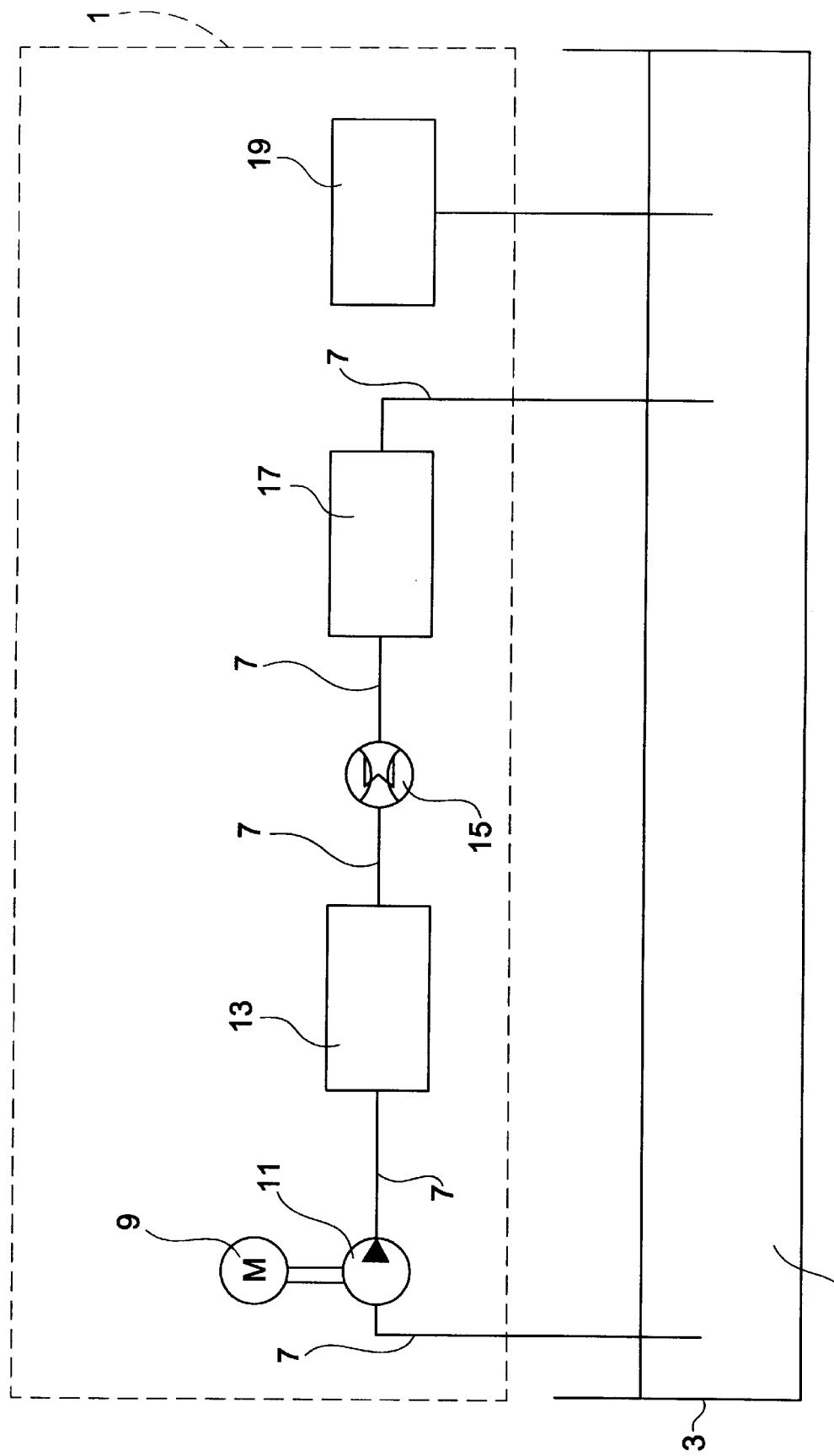
FIG. 1 is a simplified diagrammatic illustration of a hydraulic circuit of a monitoring arrangement according to one embodiment the present invention.

A structural unit 1, shown within the broken line in FIG. 1, incorporates the components of the monitoring arrangement. It is provided to fit in a tank 3 which caries a pressure fluid 5 for a fluid-technical installation. Structural unit 1 includes flow channels 7, forming a hydraulic series connection, in order. By means of a pump 11 driven by an electric motor 9, a fluid stream can flow through a particle Sensor 13, a friction wheel sensor 15 with an integrated brake coil 43 and a moisture sensor 17, one after the other. A pressure sensor 19 is also shown, which immersed in fluid 5, serves for determination of the filing level in tank 3.

Figure 2:
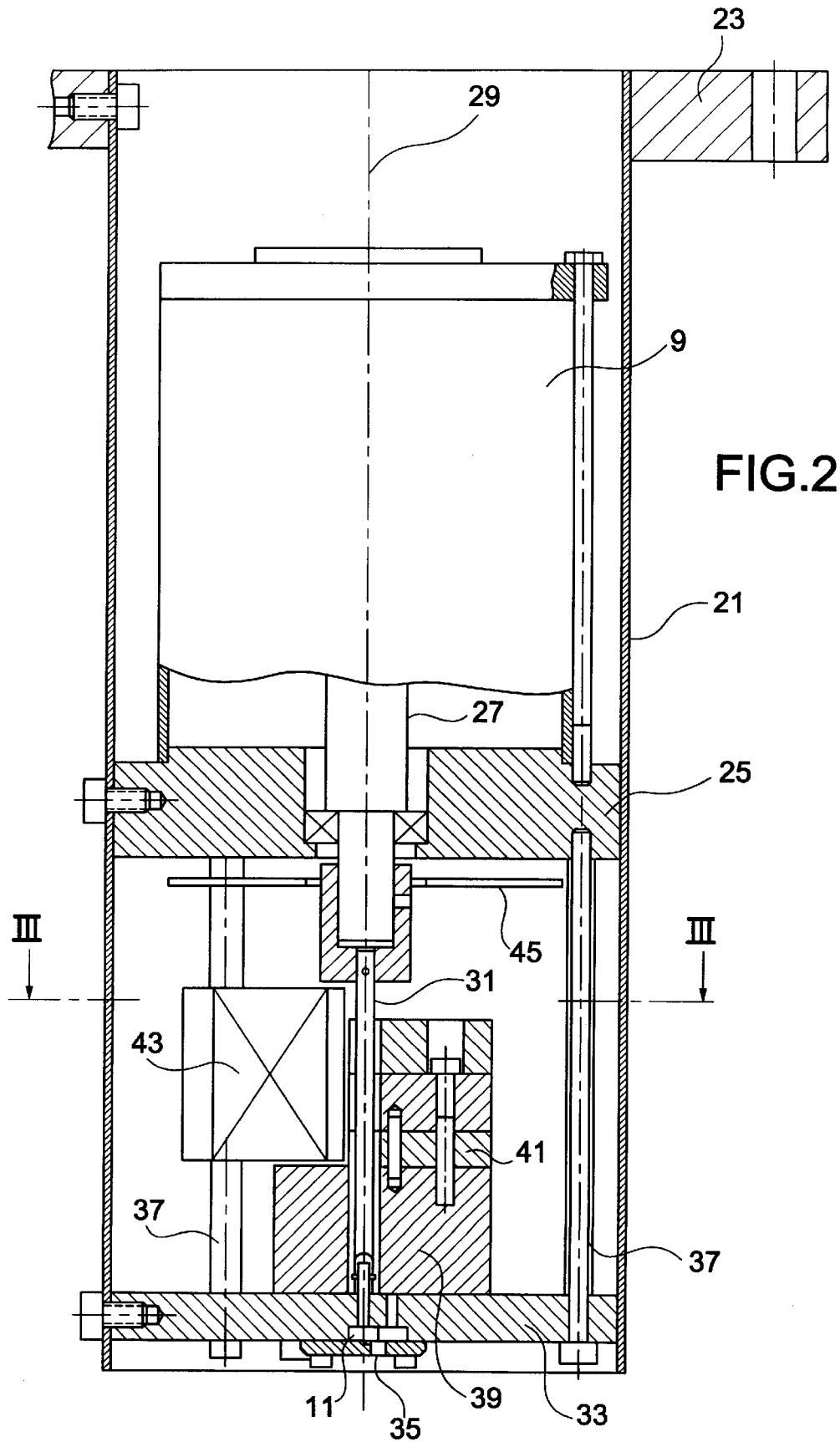
FIG. 2 is a simplified, diagrammatic side elevational view, in section, of the monitoring arrangement of FIG. 1, shown partially opened.
Figure 3:
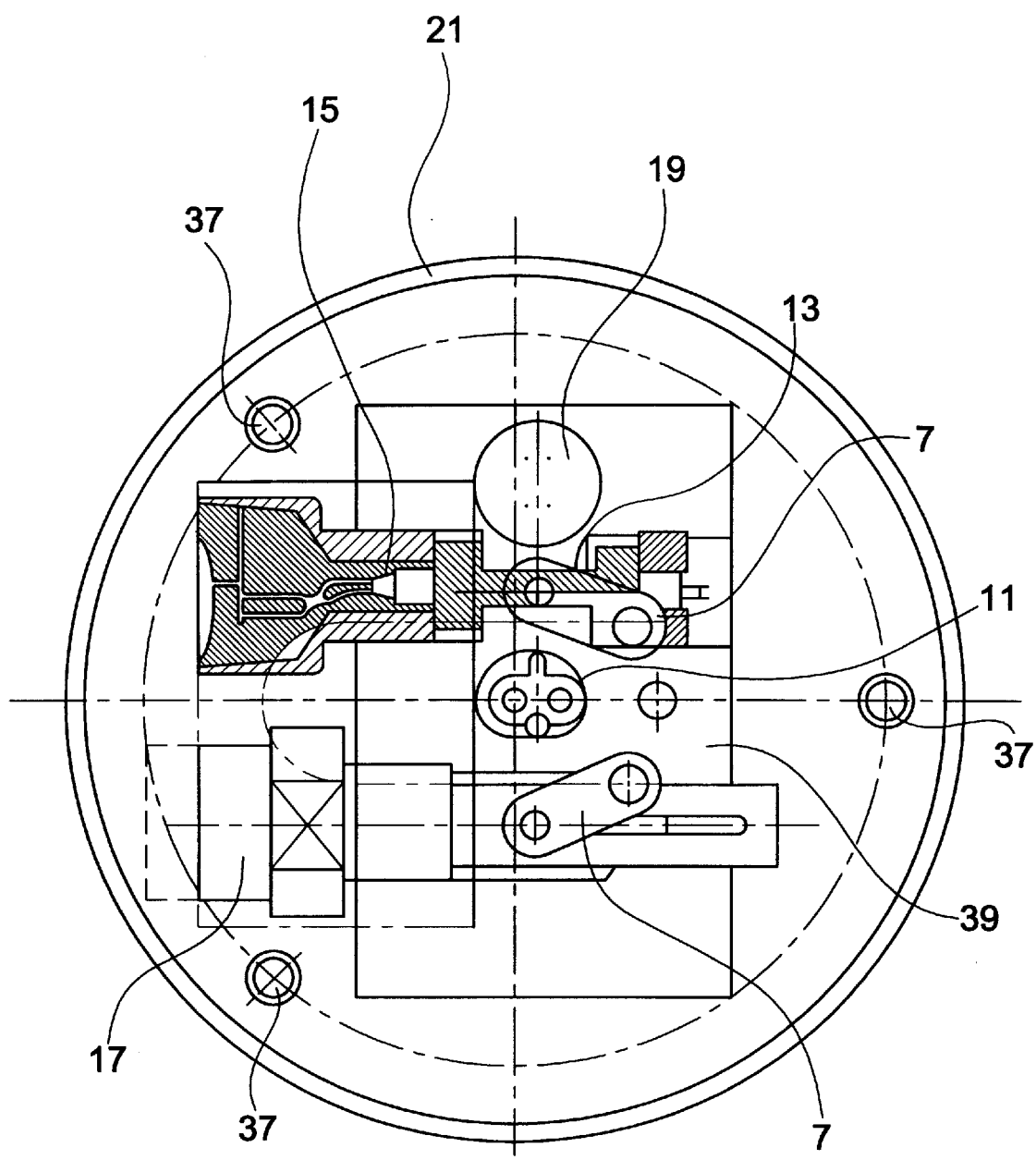
FIG. 3 is a top plan view, in section, of the monitoring arrangement taken along line III—III of FIG. 2.

As shown in FIGS. 2 and 3, structural unit 1 has a tubular frame 21, which can be screwed in and out by means of a tightening flange 23 mounted at its top end, in cooperation with the edge of an opening in the top wall of tank 3. In this manner, frame 21 extends into tank 3 and is immersed in the pressure fluid 5 in tank 3. In the exemplary embodiment, frame 21 is formed of a rigid metal-protecting cage. It represents an open structural part for the inlet of fluid 5.

The motor 9 operating pump 11 is configured as a motor adapted to be able to work immersed in fluid or oil, together with its bearing bracket or plate 25. Motor 9 is mounted by being screwed in approximately at mid-level of tubular frame 21. Its motor shaft 27 extends coaxially to the longitudinal axis 29 of frame 21. A further extension 31 of motor shaft 27 is coupled with the drive end of pump 11. The pump is a geared pump located in a base plate 33 at the bottom of the tubular frame 21. The low pressure side/ suction side inlet opening 35 of the pump is immersed in the pressure fluid 5 in tank 3.

A screw attachment connects base plate 33 with bearing bracket or plate 25 by means of threaded bolt 37. Tubular frame 21 is then configured as a metal-protecting cage, providing a mechanically rigid structure.

A sensor block 39 is mounted on the top of base plate 33, and carries the sensors indicated in FIG. 1, including particle sensor 13, friction wheel sensor 15, moisture sensor 17 and pressure sensor 19. Sensor block 39, together with an intermediate plate 41, also carries the flow channels 7 in its interior, in order, starting from the pressure-generating side of geared pump 11, to produce the hydraulic series connection through sensors 13, 15 and 17 for the fluid passage.

With the present exemplary embodiment, a particle counter of the type disclosed in EP 0 427 908 B1 is provided as particle sensor 13. The friction wheel sensor 15 serving as the viscometer is of the type disclosed in EP 0 446 246 B1 with a brake coil 43, which can be selectively activated and deactivated. When brake coil 43 is deactivated, this sensor can also serve for determination of the flow rate.

A sensor distributed by Firma Michell Instruments under the reference TDT 300 is provided as moisture sensor 17. It includes an integrated thermistor (NTC-resistance) for determination of the temperature.

Pressure sensor 19 is a piezoresistant sensor, such as is distributed by Firma Alcatel SEL under the reference DS1.

A sensor attachment plate bar 45 is mounted beneath bearing bracket or plate 25, and supports the electronic system for evaluating and processing the sensor signals. Like electric motor 9 which is configured as an immersion motor, this sensor attachment plate bar is designed for operation immersed in pressure fluid 5. The interdigital capacitors, which are part of the electronic system for evaluation of the dielectric constant of pressure fluid 5 and of its corrosion effect on copper, remain in direct contact with pressure fluid 5.

The electronic system on sensor attachment plate bar 45 supplies standardized data compatible across different systems for control of the operation of the relevant fluid-technical installation. For example, the control can be through a computer or micro-computer serving as the process control computer.

While a particular embodiment has been chosen to illustrate the invention, it will be understood by those skilled in the art that various changes and modifications can be made therein without departing from the scope of the invention as defined in the appended claims.

What is claimed is:

1. An arrangement for monitoring useful fluid properties, comprising:

a container containing a fluid to be monitored and having a container opening;

a tubular frame extending through said container opening and into said container for immersion in said fluid, said frame having frame openings for said fluid to pass therethrough;

a fluid pump with a driving motor mounted on said frame and immersed in said fluid;

a sensor block housing and integrating a plurality of fluid property sensors and flow channels connecting said sensors in series with one another and with said fluid pump, said sensor block being mounted on said frame and immersed in said fluid; and a sensor attachment plate bar arranged within said frame, carrying an electronic assembly for processing signals from said sensors, and immersed in said fluid.

2. An arrangement according to claim 1 wherein said sensors comprise a particle sensor and a viscometer.

3. An arrangement according to claim 1 wherein said sensor comprise a moisture sensor.

4. An arrangement according to claim 3 wherein said moisture sensor comprises a temperature sensor with an integrated thermistor.

5. An arrangement according to claim 2 wherein said viscometer comprises a friction wheel sensor with a brake device.

6. An arrangement according to claim 1 wherein a pressure sensor for evaluating fill levels of said fluid in said container is mounted on said frame.

7. An arrangement according to claim 1 wherein said sensor attachment plate bar comprises an interdigital capacitor for evaluating dielectric constants of said fluid.

8. An arrangement according to claim 7 wherein said sensor attachment bar comprises an interdigital capacitor of copper conductive strips for evaluating corrosion effects on copper of said fluid.

* * * * *